(12) United States Patent
Zhou et al.

(10) Patent No.: US 11,137,273 B2
(45) Date of Patent: Oct. 5, 2021

(54) GAS DETECTOR MOUNTING DESIGN

(71) Applicant: Honeywell International Inc., Morris Plains, NJ (US)

(72) Inventors: Weimin Zhou, Shanghai (CN); Zhao Xia Jin, Shanghai (CN); Rocky Qu, Shanghai (CN); Mark Li, Shanghai (CN)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 250 days.

(21) Appl. No.: 16/234,995

(22) Filed: Dec. 28, 2018

(65) Prior Publication Data
US 2019/0204122 A1 Jul. 4, 2019

(30) Foreign Application Priority Data
Dec. 29, 2017 (CN) .......................... 201711481925.2

(51) Int. Cl.
*G01D 11/30* (2006.01)
*G01D 11/24* (2006.01)
*G01N 33/00* (2006.01)

(52) U.S. Cl.
CPC ........... *G01D 11/30* (2013.01); *G01D 11/245* (2013.01); *G01N 33/0009* (2013.01)

(58) Field of Classification Search
CPC ... G01D 11/30; G01D 11/245; G01N 33/0009
See application file for complete search history.

(56) References Cited

U.S. PATENT DOCUMENTS

| 6,100,816 | A | * | 8/2000 | Moore | ................. G01R 22/065 |
| | | | | | 340/870.02 |
| 7,059,200 | B2 | * | 6/2006 | Sallee | ....................... G01F 3/10 |
| | | | | | 73/861.88 |
| 2005/0247122 | A1 | * | 11/2005 | Sallee | ..................... G01F 15/06 |
| | | | | | 73/273 |

OTHER PUBLICATIONS

Det-Tronics, Instructions Nanotechnology Metal Oxide Semiconductor (NTMOS) H2S Gas Detector, 2017 Copyright, Detector Electronics Corporation, 19 pages, Jul 29, 2020.

(Continued)

*Primary Examiner* — Jamel E Williams
(74) *Attorney, Agent, or Firm* — Alston & Bird LLP

(57) ABSTRACT

Embodiments relate generally to a gas detector system. The gas detector system comprises a gas detector mounting flange, where the gas detector mounting flange comprises an explosion-proof cylindrical body that is configured to couple the gas detector mounting flange to a gas detector and a plurality of bolt receiving slots configured to couple the gas detector mounting flange to a mounting system by securing bolts, where each bolt receiving slot is at least three times as long as a diameter of securing bolts.

20 Claims, 7 Drawing Sheets

(56) References Cited

OTHER PUBLICATIONS

ESP Saftey Inc., VECTOR Gas Detector, dated at least as early as Dec. 27, 2017, publication undated, Specification Sheet, 2 pages, http://www.espsafetyinc.com/toxic-gas-detector.php, Jul. 29, 2020.
Net Safety Monitoring Inc., Millennium II Basic Gas Detection Transmitter (M2B Transmitter), Single Channel Universal Gas Monitoring, Sep. 1, 2014, Product Data Sheet, 4 pages, http://vertassets.blob.core.windows.net/download/3c196736/3c196736-0007-4c66-99a3-2abd96988e62/fgd_pds_m2b_basic_gas_detection_transmitter.pdf, Jul. 29, 2020.
VEGA Grieshaber KG, VEGADIS 82, External Display and Adjustment Unit for PLICS Sensors, Mar. 8, 2018, Specification Sheet, 2 pages, https://www.vega.com/en/products/product-catalog/signal-conditioning/indicating-instruments/vegadis-81, Jul. 29, 2020.

* cited by examiner

GAS DETECTOR MOUNTING DESIGN

CROSS-REFERENCE TO RELATED APPLICATIONS

The present application claims priority to Chinese Patent Application No. 201711481925.2 filed Dec. 29, 2017 by Weimin Zhou, et al. and entitled "Gas Detector Mounting Design," which is incorporated by reference herein in its entirety.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Gas detectors may be statically placed in an environment to detect the presence of gas, for example hazardous gas, and generate an alert and/or report to a monitoring station. The gas detectors may be explosion-proof. The gas detectors may be coupled to a mounting flange that may be used to attach the gas detector to the structure of the environment.

SUMMARY

In an embodiment a gas detector system is disclosed. The gas detector system comprises a gas detector mounting flange, where the gas detector mounting flange comprises an explosion-proof cylindrical body that is configured to couple the gas detector mounting flange to a gas detector and a plurality of bolt receiving slots configured to couple the gas detector mounting flange to a mounting system by securing bolts, where each bolt receiving slot is at least three times as long as a diameter of securing bolts.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The following brief definition of terms shall apply throughout the application:

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example;

The terms "about" or "approximately" or the like, when used with a number, may mean that specific number, or alternatively, a range in proximity to the specific number, as understood by persons of skill in the art field; and If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

Embodiments of the disclosure include a gas detector system that comprises a mounting flange that promotes flexibility in mounting the gas detector system to a structure in an environment, for example to a vertical post in the environment such as an oil refinery environment, a chemical processing plant environment, a gas handling plant environment, or other industrial environment. In some gas detector systems a mounting flange may have narrow holes that entail precise alignment of the mounting flange to a mounting plate or other mounting hardware that is attached to a structure in the environment. This can result in a problem when such precise alignment of the mounting flange is not compatible with the mounting plate or mounting hardware in the given environment. This disclosure provides a technical solution to this technical problem by teaching about a mounting flange that defines slots that mate with mounting bolts in a variety of different positions not just one precise alignment of mounting bolts.

Figure 1:
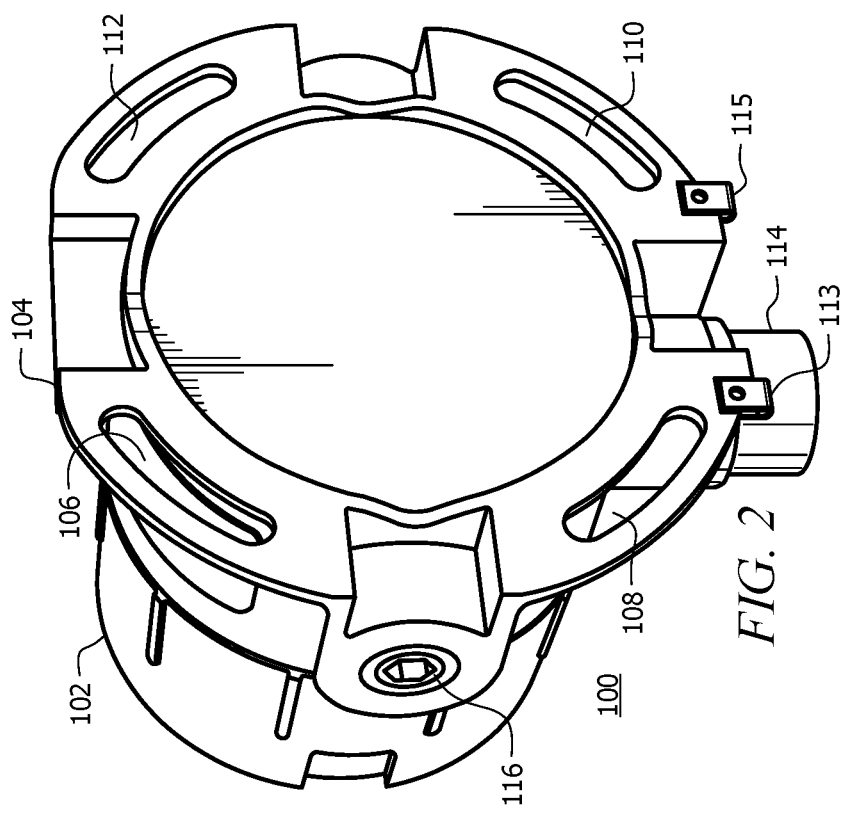
FIG. 1 illustrates a gas detector system according to an embodiment of the disclosure.
Figure 2:
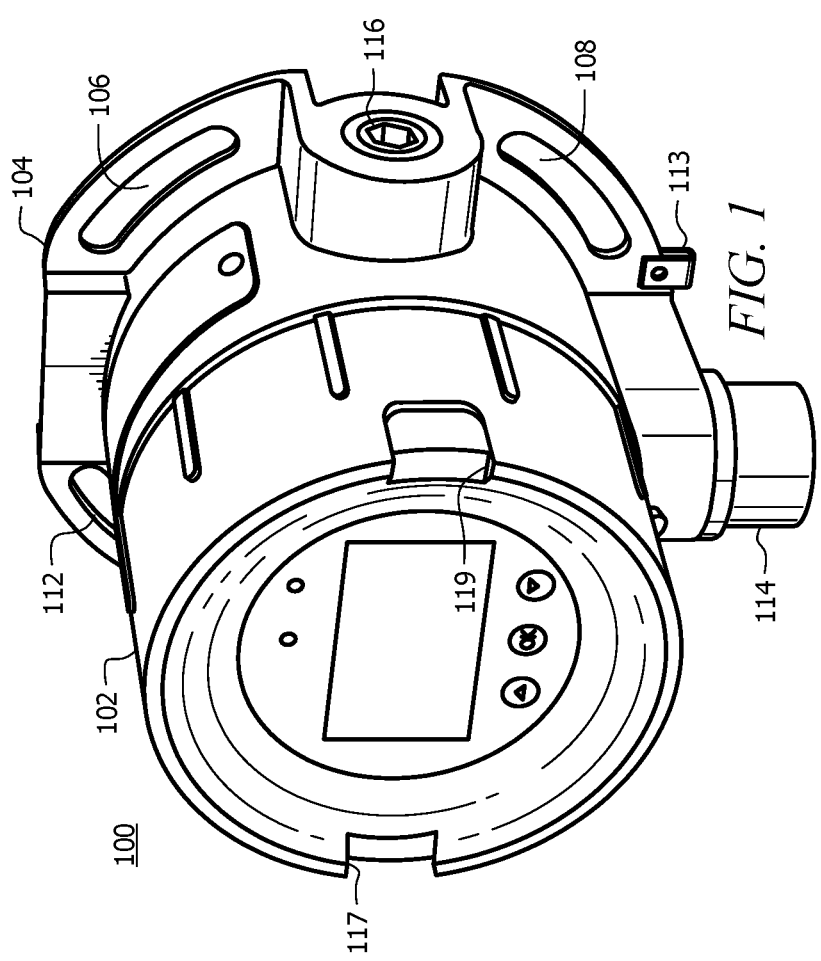
FIG. 2 illustrates a gas detector system from another view according to an embodiment of the disclosure.
Figure 3:
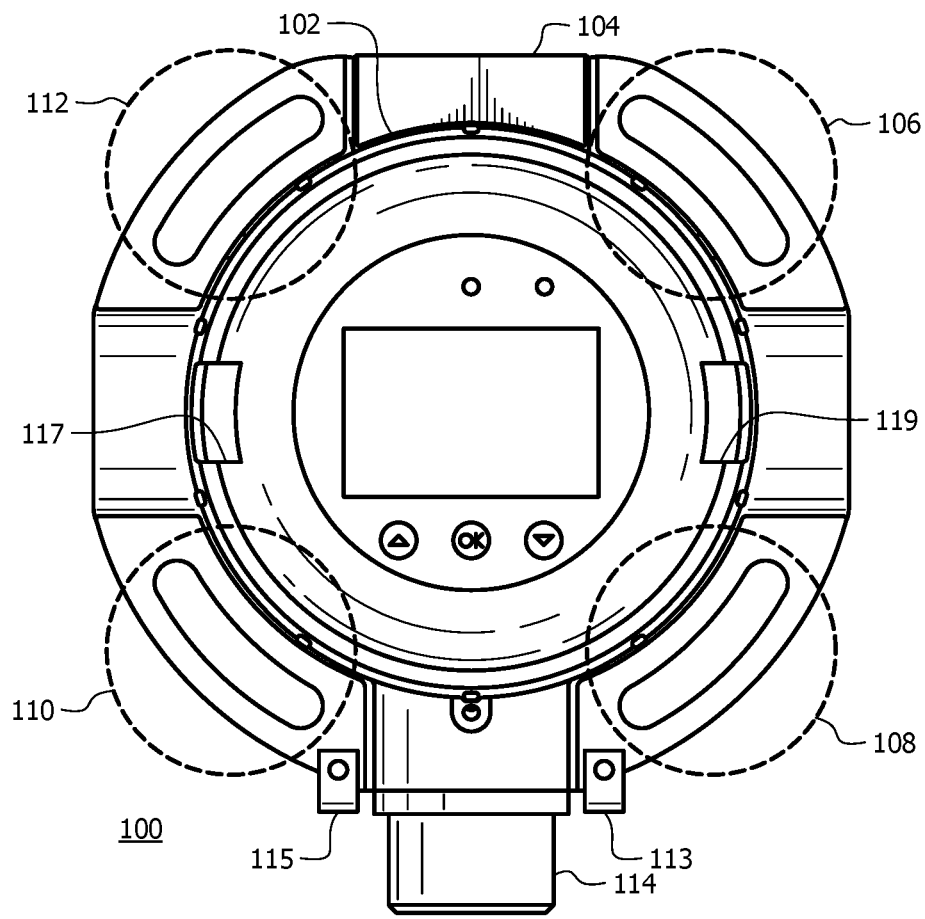
FIG. 3 illustrates a mounting flange of the gas detector system according to an embodiment of the disclosure.

Referring now to FIG. 1, FIG. 2, and FIG. 3, a gas detector system 100 is described. In an embodiment, the system 100 comprises a gas detector 102 and a mounting flange 104. In some contexts, the mounting flange 104 may be referred to as a gas detector mounting flange. In an embodiment, the gas detector 102 may be an explosion-proof gas detector 102, for example an explosion-proof gas detector suitable for use in an environment where combustible gas may sometimes be present, for example when combustible gas escapes from a leak or when a gas reservoir or conduit is accidentally broken. In this embodiment, the mounting flange 104 may likewise be an explosion-proof mounting flange 104. Standards for explosion-proof equipment may define a maximum pressure that the equipment must be capable of sustaining without failure and may define that the explosion-proof equipment block propagation of explosion and/or propagation of a flame both from an exterior of the equipment to an interior of the equipment and from an interior of the equipment to an exterior of the equipment.

The mounting flange 104 has a cylindrical body and comprises two or more bolt receiving slots, for example a first bolt receiving slot 106, a second bolt receiving slot 108, a third bolt receiving slot 110, and a fourth bolt receiving slot 112. The bolt receiving slots 106, 108, 110, 112 are banana-shaped or arc shaped. In an embodiment, a center line of the slots 106, 108, 110, 112 may be located approximately on the same perimeter of an imagined circle centered on a central axis of the cylindrical body of the mounting flange 104. The arc length of each of the slots 106, 108, 110, 112 may be at least three times a diameter of a bolt configured to pass through the slots and attach the mounting flange 104 and the gas detector system to a structure in the environment. In an embodiment the arc length of each of the slots 106, 108, 110, 112 is at least four times a diameter of a bolt configured to pass through the slots and attach the mounting flange 104 and the gas detector system to a structure in the environment. The arc length of the receiving slots 106, 108, 110, 112 promotes flexibility of alignment of the mounting flange 104 and the gas detector system 100 with a structure in the environment, for example flexibility of alignment of the mounting flange 104 with reference to a mounting plate discussed further hereinafter.

The mounting flange 104 may further comprise a sensor connection or connection port 114 and a cable connection port 116 which provide access to an interior of the mounting flange 104 to connect external gas sensor inputs and electrical cables to the electronics and/or printed circuit board (PCB) of the gas detector 102. The mounting flange 104, in an embodiment, may comprise one or more grounding clips 113, 115 for grounding the mounting flange 104 and the gas detector sensor system 100 to the environment. The gas detector 102 may comprise a housing defining a slot 117, 119 that may mate with a tool such as a lever to tighten the gas detector 102 in threaded coupling with the mounting flange 104 and/or to loosen the gas detector 102 from threaded coupling with the mounting flange 104. Said in another way, in an embodiment, the mounting flange 104 is configured to threadingly couple to the gas detector 102.

Figure 4:
FIG. 4 illustrates a first bolt hole pattern of a mounting flange.

Turning now to FIG. 4, an example of a bolt hole pattern of a mounting flange different from the mounting flange 104 taught herein. The bolt hole pattern includes a first bolt hole 120, a second bolt hole 122, a third bolt hole 124, and a fourth bolt hole 126. Visual inspection of this bolt hole pattern reveals that a mounting flange having this bolt hole pattern for attaching to a structure in the environment, for example for attaching to a mounting plate attached to a structure in the environment, provides substantially no flexibility for positioning of the mounting flange. If the bolt hole pattern of FIG. 4 does not align nearly exactly with the environment, the mounting flange and gas detector system cannot be mounted!

Figure 5:
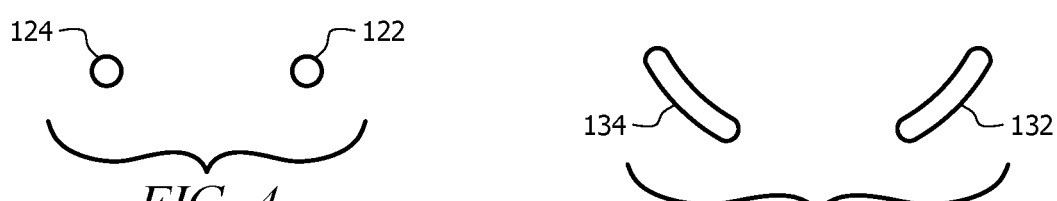
FIG. 5 illustrates a second bolt hole pattern of a mounting flange according to an embodiment of the disclosure.
Figure 8:
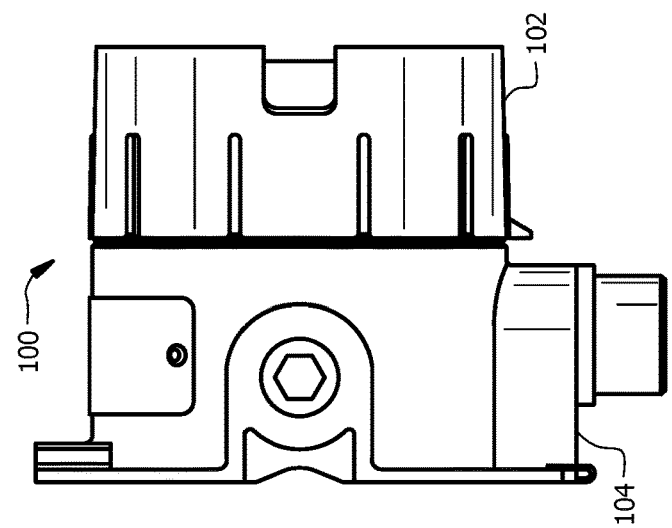
FIG. 8 illustrates an opposite side view of a gas detector system according to an embodiment of the disclosure.
Figure 7:
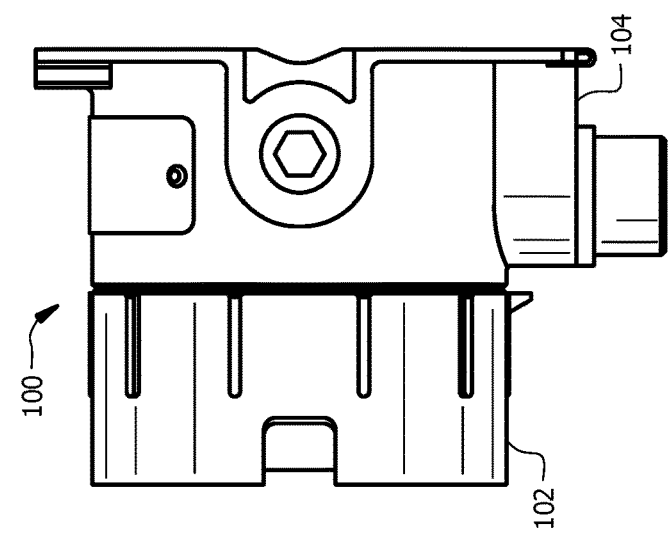
FIG. 7 illustrates a first side view of a gas detector system according to an embodiment of the disclosure.
Figure 6:
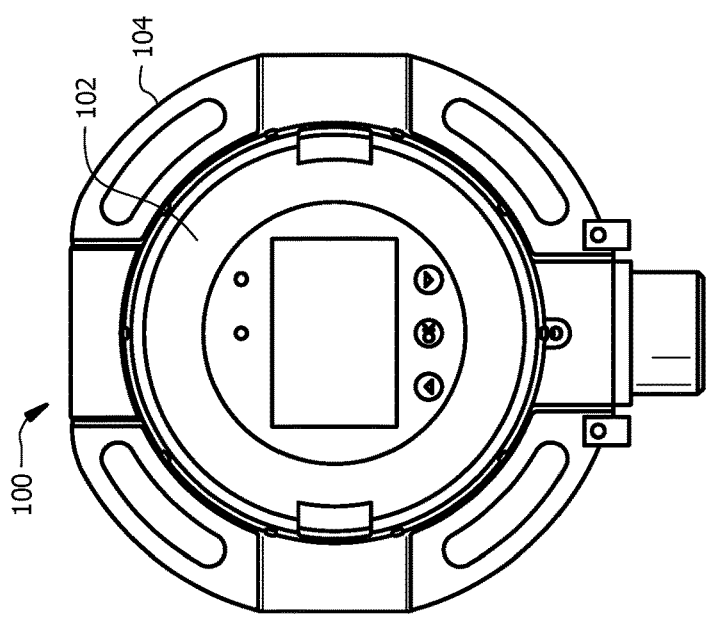
FIG. 6 illustrates a front view of a gas detector system according to an embodiment of the disclosure.
Figure 11:
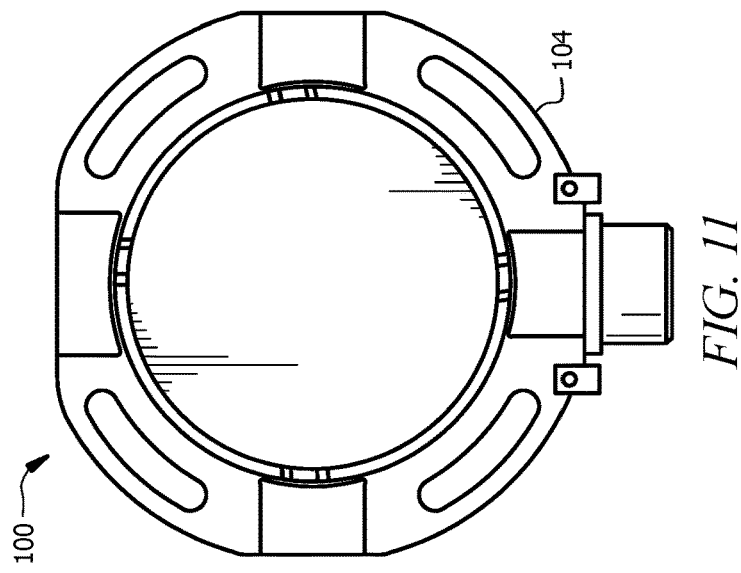
FIG. 11 illustrates a back view of a gas detector system according to an embodiment of the disclosure.
Figure 10:
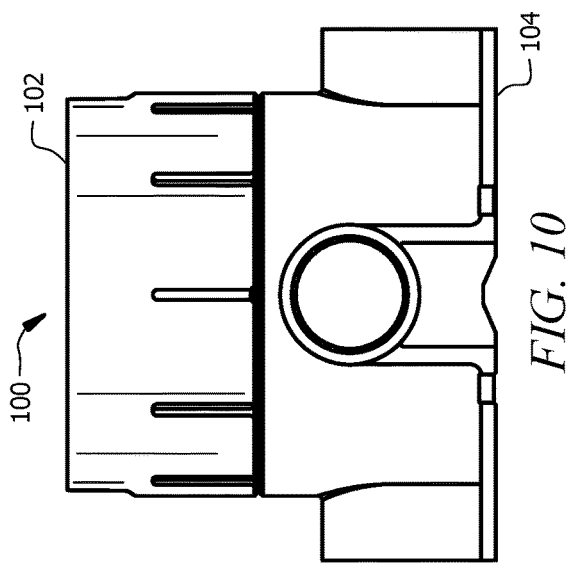
FIG. 10 illustrates a bottom view of a gas detector system according to an embodiment of the disclosure.
Figure 9:
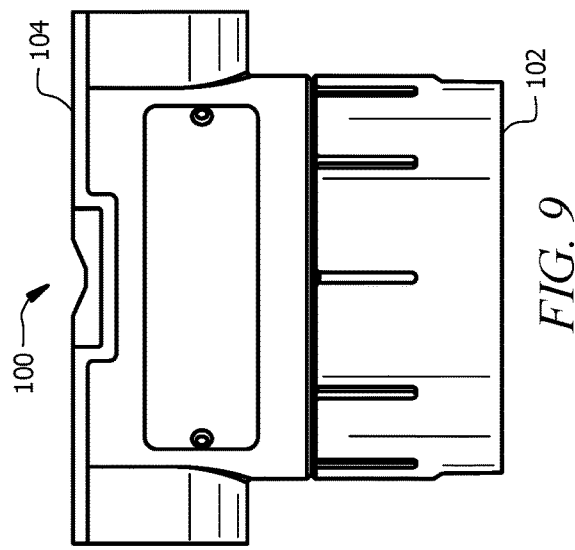
FIG. 9 illustrates a top view of a gas detector system according to an embodiment of the disclosure.

Turning now to FIG. 5, a bolt hole pattern of the mounting flange 104 is illustrated for contrast with the bolt hole pattern of FIG. 4. The bolt hole pattern features a first bolt receiving slot 130, a second bolt receiving slot 132, a third bolt receiving slot 134, and a fourth bolt receiving slot 136 (corresponding to bolt receiving slots 106, 108, 110, and 112 of the mounting flange 104 respectively). Visual inspection of the bolt hole pattern of FIG. 5 reveals that a mounting flange having this bolt hole pattern provides considerable flexibility for positioning of the mounting flange relative to securing bolts and attaching to a structure in the environment.

Turning now to FIG. 6, FIG. 7, FIG. 8, FIG. 9, FIG. 10, and FIG. 11, different views of the mounting flange 104 are illustrated.

Figure 12:
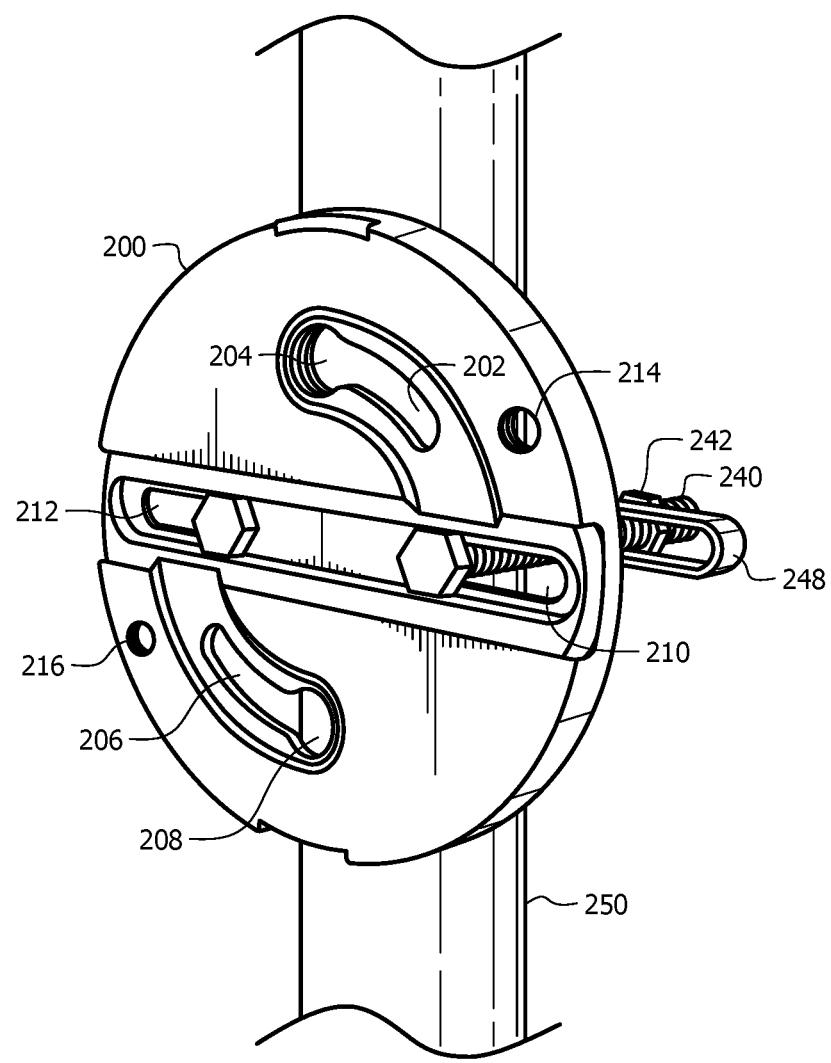
FIG. 12 illustrates a mounting plate for mounting a gas detector system to a structure in an environment according to an embodiment of the disclosure.

Turning now to FIG. 12, a mounting plate 200 is described. In an embodiment, the mounting plate 200 defines a first slot 202 and a second slot 206 configured to receive locating lugs of a mounting flange. The first slot 202 has a first opening 204 that is configured to allow the passage of a head of a locating lug while the rest of the first slot 202 is narrower and configured to capture and retain the head of the locating lug. The second slot 206 has a second opening 208 that is configured to allow the passage of a head of a locating lug while the rest of the second slot 206 is narrower and configured to capture and retain the head of the locating lug. In an embodiment, the mounting plate 200 further defines a third slot 210 configured to receive a bolt coupled to a mounting strap and a fourth slot 212 configured to receive a bolt 240 coupled to a mounting strap 248 and secured by a nut 242. In an embodiment, the mounting plate 200 defines a first threaded hole 214 and a second threaded hole 216. A securing bolt (not shown) may be inserted through one of the bolt receiving slots 106, 108, 110, 112 and threaded into one of the holes 214, 216 to secure the mounting flange 104 and the gas detector 102 to the mounting plate 200 and thus secure the gas detector 102 to structure in the environment. In an embodiment, mounting lugs of the mounting flange 104 are first passed through the openings 204, 208, the mounting flange 104 and mounting lugs are rotated with respect to the mounting plate 200 to align the mounting flange 104, and then two securing bolts are passed through two of the bolt receiving slots 106, 108, 110, 112 and threaded into the threaded holes 214, 216.

Figure 13:
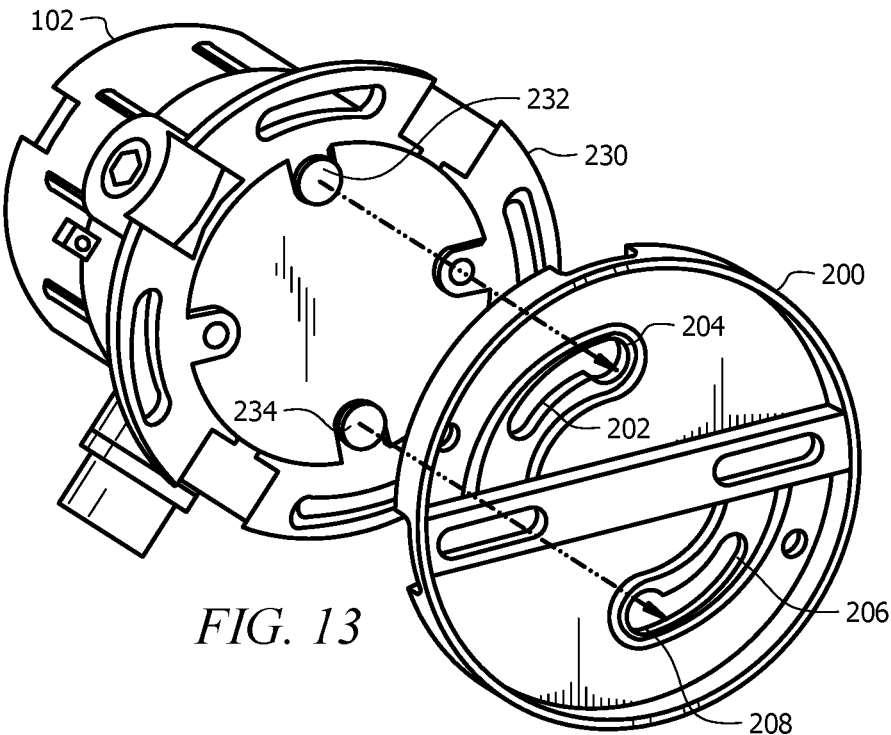
FIG. 13, FIG. 14, and FIG. 15 illustrate coupling a mounting flange of a gas detector system to a mounting plate according to an embodiment of the disclosure.
Figure 14:
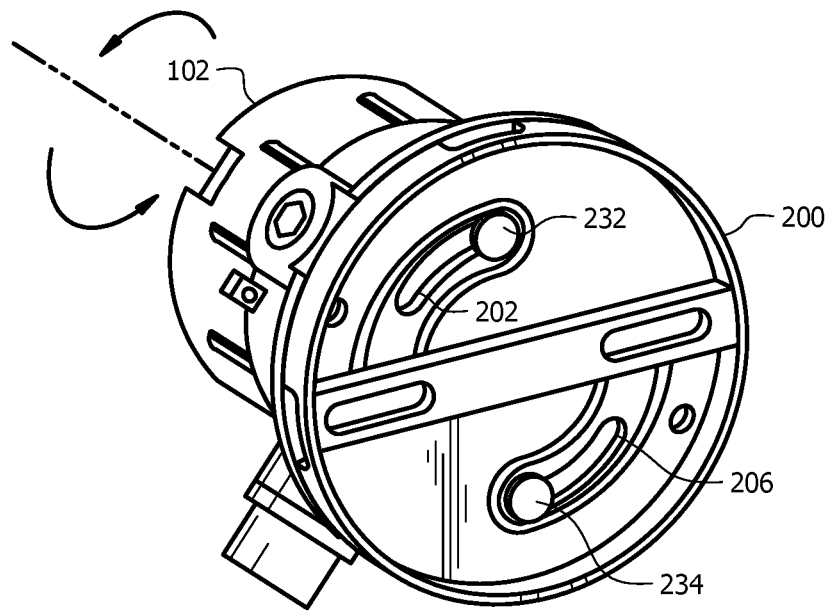
Figure 15:
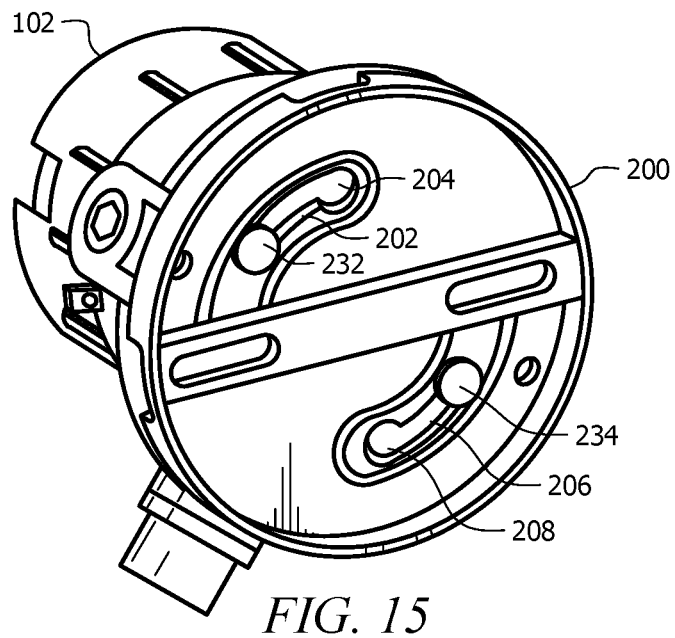

Turning now to FIG. 13, FIG. 14, and FIG. 15, a mounting flange 230 is described. The mounting flange 230 is substantially similar to the mounting flange 104 described above, with the exception that the mounting flange 230 further comprises a first locating lug 232 and a second locating lug 234. The locating lugs 232, 234 comprise a post that has a smaller diameter than the width of the slots 202, 206 and a head that is smaller in diameter than the openings 204, 208 but larger in diameter than the width of the slots 202, 206, whereby the slots 202, 206 are configured to capture and retain the posts of the locating lugs 232, 234 when the mounting flange 230 is rotated with reference to the mounting plate 200.

Figure 16:
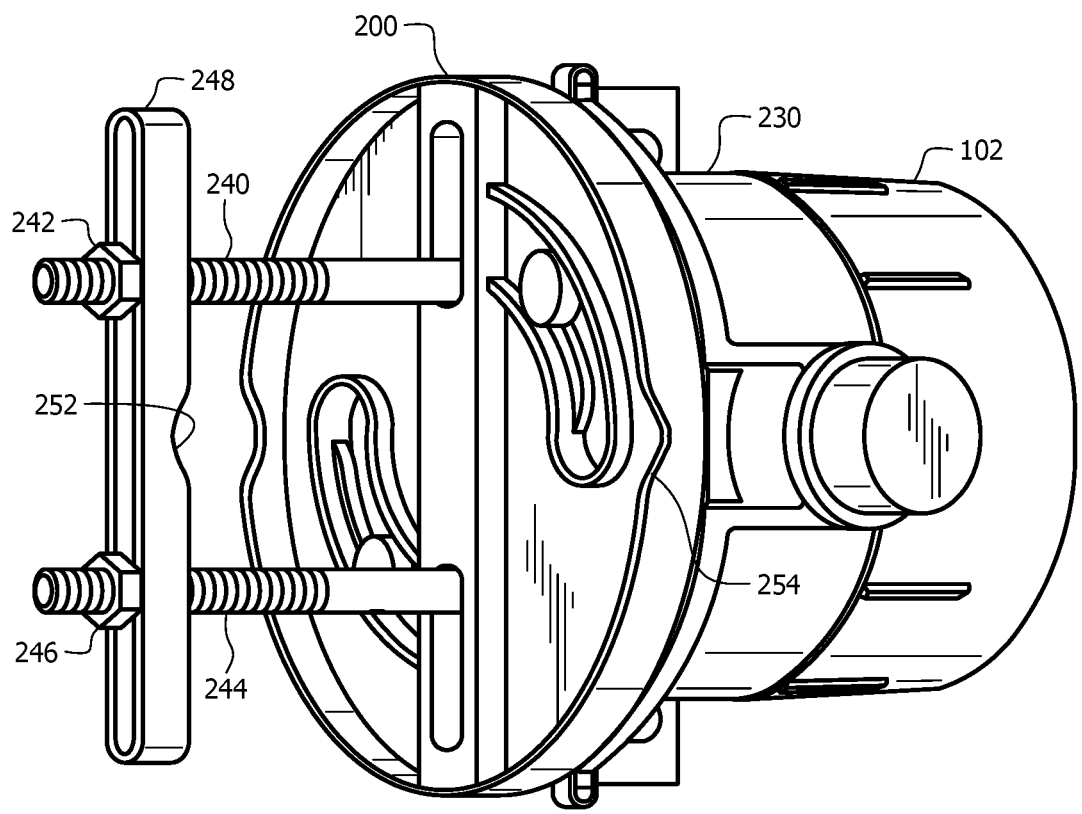
FIG. 16 illustrates mounting hardware for attaching a mounting plate and gas detector system to a structure in an environment according to an embodiment of the disclosure.

Turning now to FIG. 16, further details of the mounting hardware are described The mounting plate 200 may be secured to a structure in the environment, for example to the post 250 illustrated in FIG. 12, by a first bolt 240 secured by a first nut 242, a second bolt 244 secured by a second nut 246, where the bolts 240, 244 pass through a securing bracket 248 at one end and at opposite ends pass through the bolt receiving slots 210, 212 to secure to the mounting plate 200. The nuts 242, 246 may be threaded and tightened so that the securing bracket 248 and the mounting plate 200 are tightly fitted to a structure in the environment, for example to a post 250 illustrated in FIG. 12. In an embodiment, a curved edge 252 of the securing bracket 248 and a corresponding curved edge 254 in the mounting plate 200 are configured to mate with a curved structure in the environment, for example to mate with the post 250 illustrated in FIG. 12.

Having described various devices and methods herein, exemplary embodiments or aspects can include, but are not limited to:

In a first embodiment, a gas detector system comprises a gas detector mounting flange. The gas detector mounting flange comprises an explosion-proof cylindrical body that is configured to couple the gas detector mounting flange to a gas detector and a plurality of bolt receiving slots configured to couple the gas detector mounting flange to a mounting system by securing bolts, where each bolt receiving slot is at least three times as long as a diameter of securing bolts.

A second embodiment can include the system of the first embodiment, wherein the plurality of bolt receiving slots is four bolt receiving slots.

A third embodiment can include the first embodiment, wherein the explosion-proof cylindrical body is configured to threadingly couple the gas detector mounting flange to the gas detector.

A fourth embodiment can include the system of the third embodiment, further comprising a gas detector coupled to the explosion-proof cylindrical body, wherein the gas detector comprises a housing defining a slot in a face of the gas detector that is configured to mate with a lever to tighten or loosen the coupling of the gas detector to the explosion-proof cylindrical body.

A fifth embodiment can include the system of the first embodiment, wherein the gas detector mounting flange further comprises a plurality of locating lugs configured to mate with a mounting plate.

A sixth embodiment can include the system of the fifth embodiment, further comprising a mounting plate that defines a plurality of slots to receive the locating lugs of the gas detector mounting flange, where the mounting plate is configured to be mounted to a structure in an environment.

A seventh embodiment can include the system of the sixth embodiment, wherein the gas detector mounting flange comprises two locating lugs and the mounting plate defines two slots to receive the locating lugs of the gas detector mounting flange.

An eighth embodiment can include the system of the sixth embodiment, wherein the mounting plate defines a plurality of threaded holes configured to receive securing bolts passed through the receiving slots of the gas detector mounting flange to secure the gas detector mounting flange to the mounting plate.

A ninth embodiment can include the system of the sixth embodiment, wherein the mounting plate further defines a plurality of slots for receiving bolts coupled to a mounting strap configured to mount the mounting plate to a structure in the environment.

A tenth embodiment can include the system of the ninth embodiment, wherein the mounting plate defines two slots for receiving bolts coupled to the mounting strap.

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow that scope including all equivalents of the subject matter of the claims. Each and every claim is incorporated as further disclosure into the specification and the claims are embodiment(s) of the present invention(s). Furthermore, any advantages and features described above may relate to specific embodiments, but shall not limit the application of such issued claims to processes and structures accomplishing any or all of the above advantages or having any or all of the above features.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure. Specifically and by way of example, although the headings might refer to a "Field," the claims should not be limited by the language chosen under this heading to describe the so-called field. Further, a description of a technology in the "Background" is not to be construed as an admission that certain technology is prior art to any invention(s) in this disclosure. Neither is the "Summary" to be considered as a limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of the claims shall be considered on their own merits in light of this disclosure, but should not be constrained by the headings set forth herein.

Use of broader terms such as "comprises," "includes," and "having" should be understood to provide support for narrower terms such as "consisting of," "consisting essentially of," and "comprised substantially of." Use of the terms "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A gas detector system, comprising:
   a gas detector mounting flange, where the gas detector mounting flange comprises
   an explosion-proof cylindrical body that is configured to couple the gas detector mounting flange to a gas detector, and
   a plurality of bolt receiving slots configured to couple the gas detector mounting flange to a mounting system by securing bolts, where each bolt receiving slot is at least three times as long as a diameter of securing bolts.

2. The gas detector system of claim 1, wherein the plurality of bolt receiving slots is four bolt receiving slots.

3. The gas detector system of claim 1, wherein the explosion-proof cylindrical body is configured to threadingly couple the gas detector mounting flange to the gas detector.

4. The gas detector system of claim 3, further comprising a gas detector coupled to the explosion-proof cylindrical body, wherein the gas detector comprises a housing defining a slot in a face of the gas detector that is configured to mate with a lever to tighten or loosen the coupling of the gas detector to the explosion-proof cylindrical body.

5. The gas detector system of claim 1, wherein the gas detector mounting flange further comprises a plurality of locating lugs configured to mate with a mounting plate.

6. The gas detector system of claim 5, further comprising a mounting plate that defines a plurality of slots to receive the locating lugs of the gas detector mounting flange, where the mounting plate is configured to be mounted to a structure in an environment.

7. The gas detector system of claim 6, wherein the gas detector mounting flange comprises two locating lugs and the mounting plate defines two slots to receive the locating lugs of the gas detector mounting flange.

8. The gas detector system of claim 6, wherein the mounting plate defines a plurality of threaded holes configured to receive securing bolts passed through the receiving slots of the gas detector mounting flange to secure the gas detector mounting flange to the mounting plate.

9. The gas detector system of claim 6, wherein the mounting plate further defines a plurality of slots for receiving bolts coupled to a mounting strap configured to mount the mounting plate to a structure in the environment.

10. The gas detector system of claim 9, wherein the mounting plate defines two slots for receiving bolts coupled to the mounting strap.

11. A gas detector system, comprising:
    a gas detector mounting flange, wherein the gas detector mounting flange comprises
    an explosion-proof cylindrical body that is configured to couple the gas detector mounting flange to a gas detector, and
    a plurality of bolt receiving slots configured to couple the gas detector mounting flange to a mounting system by securing bolts, where each bolt receiving slot is longer than a diameter of securing bolts.

12. The gas detector system of claim 11, wherein the plurality of bolt receiving slots is four bolt receiving slots.

13. The gas detector system of claim 11, wherein the explosion-proof cylindrical body is configured to threadingly couple the gas detector mounting flange to the gas detector.

14. The gas detector system of claim 13, further comprising a gas detector coupled to the explosion-proof cylindrical body, wherein the gas detector comprises a housing defining a slot in a face of the gas detector that is configured to mate with a lever to tighten or loosen the coupling of the gas detector to the explosion-proof cylindrical body.

15. The gas detector system of claim 14, wherein the gas detector mounting flange further comprises a plurality of locating lugs configured to mate with a mounting plate.

16. The gas detector system of claim 15, further comprising a mounting plate that defines a plurality of slots to receive the locating lugs of the gas detector mounting flange, where the mounting plate is configured to be mounted to a structure in an environment.

17. The gas detector system of claim 16, wherein the gas detector mounting flange comprises two locating lugs and the mounting plate defines two slots to receive the locating lugs of the gas detector mounting flange.

18. The gas detector system of claim 16, wherein the mounting plate defines a plurality of threaded holes configured to receive securing bolts passed through the receiving slots of the gas detector mounting flange to secure the gas detector mounting flange to the mounting plate.

19. The gas detector system of claim 16, wherein the mounting plate further defines a plurality of slots for receiving bolts coupled to a mounting strap configured to mount the mounting plate to a structure in the environment.

20. A gas detector system, comprising:
    a gas detector mounting flange, wherein the gas detector mounting flange comprises
    an explosion-proof cylindrical body that is configured to couple the gas detector mounting flange to a gas detector, and
    a plurality of bolt receiving slots configured to couple the gas detector mounting flange to a mounting system by securing bolts, wherein at least one bolt receiving slot is longer than a diameter of securing bolts.

* * * * *